United States Patent [19]
Sudhölter et al.

[11] Patent Number: 4,882,292
[45] Date of Patent: Nov. 21, 1989

[54] PROCESS FOR MANUFACTURING A REFET OR A CHEMFET, AND THE MANUFACTURED REFET OR CHEMFET

[75] Inventors: Ernst J. Sudhölter, Losser; Maria D. Skowronska-Ptasinska, Enschede; Peter D. Van der Wal, Enschede; Albert Van den Berg, Enschede; David N. Reinhoudt, Hengelo, all of Netherlands

[73] Assignee: Stichting Centrum voor Micro-Elektronics Twente, Enschede, Netherlands

[21] Appl. No.: 93,014

[22] Filed: Sep. 4, 1987

[30] Foreign Application Priority Data

Sep. 5, 1986 [NL] Netherlands ............. 8602242

[51] Int. Cl.$^4$ ............. G01N 27/00; H01L 29/28
[52] U.S. Cl. ............. 437/42; 437/235; 204/418; 357/25
[58] Field of Search ............. 437/1, 42, 235; 357/25, 357/8, 23.15; 204/418

[56] References Cited

U.S. PATENT DOCUMENTS

| 4,269,682 | 5/1981 | Yano et al. | 204/418 |
| 4,305,802 | 12/1981 | Koshiishi | 357/25 |
| 4,490,216 | 12/1984 | McConnell | 357/25 |
| 4,650,547 | 3/1987 | Gough | 204/418 |
| 4,816,118 | 3/1989 | Oyama et al. | 204/418 |

FOREIGN PATENT DOCUMENTS

| 0158834 | 3/1985 | European Pat. Off. . | |
| 56-2546 | 1/1981 | Japan | 357/25 |
| 59-182356 | 10/1984 | Japan | 204/418 |
| 8504480 | 10/1985 | PCT Int'l Appl. . | |

Primary Examiner—Olik Chaudhuri
Attorney, Agent, or Firm—Webb, Burden, Ziesenheim & Webb

[57] ABSTRACT

The invention relates to a process for manufacturing a REFET and/or CHEMFET, comprising: (a) covalent bonding of a hydrophilic polymer layer to an isolator layer applied to a semiconductor material; (b) the absorption of water or a watery solution into said hydrophilic polymer layer; and (c) the binding of a hydrophobic polymer layer to the water holding hydrophilic polymer layer. It is advantageous that this water holding hydrophilic polymer layer also contains an electrolyte and/or a buffer.

Preferably an ion to be measured with the CHEMFET also forms part of the electrolyte.

21 Claims, No Drawings

PROCESS FOR MANUFACTURING A REFET OR A CHEMFET, AND THE MANUFACTURED REFET OR CHEMFET

The current invention relates to the manufacture of a REFET when an ISFET is coated with an inert hydrophobic layer, or of a CHEMFET, when an ISFET is modified with a hydrophobic layer, which contains a receptor molecule for a chemical compound to be measured, for example a cation, anion, proton, urea, sugar, protein, antibody, antigen. By ISFET (Ion Sensitive Field Effect Transistor) is understood a semiconductor material provided with an isolator layer. The ISFETs are made in accordance with standard MOS technology. The isolator layer is thermally deposited at 1150° C. for 15 min. in an $O_2$ atmosphere. The layer thickness amount to ca. 700 Å.

Compared to the conventional ion selective electrodes, REFET and CHEMFET possess a number of advantages:

(1) they are small and therefore possibly suitable for biomedical applications;
(2) they are robust;
(3) they can be manufactured using IC technology, thereby enabling the manufacture of a miniature multi-sensor;
(4) mass production at low cost is possible without problem;
(5) as a result of the low output impedance the sensitivity to external interference signals is smaller; and
(6) they possess a better signal-to-noise ratio.

The isolator layer or insulating layer (usually designated as gate-oxide layer) applied to the semiconductor material can for example consist either of layers of $SiO_2$, $Al_2O_3$, $Ta_2O_5$, $TiO_2$, $ZrO_2$ and/or $Si_3N_4$ (not an oxide!) or of a layered structure consisting of materials differing from one another.

The exterior surface of the isolator layer contains chemically reactive, particularly protonic groups (silanol groups in the case of $SiO_2$ and amine groups in the case of $Si_3N_4$). These groups ensure that the chemically non-modified ISFET gives response to the changes in the proton concentration. It is desirable for the measurement of other chemical compounds to take steps in order to suppress or entirely eliminate this proton sensitivity. These steps can consist of allowing these reactive groups to react, as a result of which the reactivity disappears, of covering the isolator layer with an inert, hydrophobic polymer, or of covalent bonding of an inert, hydrophobic polymer to the isolator layer. This latter possibility is comprehensively described in the international patent application WO 85/04480 in the name of applicant, the Stichting Centrum voor Micro-Electronics Twente of Enschede.

If the hydrophobic polymer contains ionophors a specific ion sensitivity and ion specificity occurs that is specifically dependent upon the ionophors. Such an ISFET is called a CHEMFET. An $H^+$ insensitive ISFET is called a REFET.

After extensive research it has been found that the characteristics of a sensor containing such as REFET and/or CHEMFET as an essential component can be markedly improved in respect of noise, drift and hysteresis. This is achieved according to the invention when a process for manufacturing such a FET comprises: (a) covalent bonding of a hydrophilic polymer layer to an isolator layer applied to a semiconductor material; (b) the absorption of water or an aqueous solution into the hydrophilic polymer layer; and (c) the binding of a hydrophobic polymer layer to the water-holding hydrophilic polymer layer. Reproducibility will moreover improve during production.

It was found during this research that many problems relating to the characteristics referred to above could be traced back to unverifiable variations in the chemical structure at the location of the interface between the isolator layer and the hydrophobic polymer layer applied thereto. These variations were inherent to the conventional fabrication methods employed.

Application of the water-holding, hydrophilic polymer layer between the isolator layer and the hydrophobic polymer layer results in thermodynamically and chemically better defined interfaces between on the one hand isolator layer and hydrophilic polymer layer and on the other between the hydrophilic polymer layer and the hydrophobic polymer layer.

The hydrophilic polymer layer should be covalently bonded to the isolator layer since otherwise a durability is achieved amounting only to several hours, which is unsuitable for practical use.

The hydrophilic polymer layer preferably also contains an electrolyte so that the fall in potential over the interface between the hydrophilic polymer layer and the hydrophobic polymer layer is determined and is virtually independent of the composition of the solution for measuring. In the case of a CHEMFET an ion to be measured with the CHEMFET preferably forms part of the electrolyte.

It is further to be recommended that the hydrophilic polymer layer also contains a buffer. In this way the pH in the hydrophilic polymer layer is kept substantially constant, also when there is penetration of $H^+$ ions or penetration of $CO_2$ through the hydrophobic polymer layer. A particularly favourable CHEMFET or REFET is obtained if the hydrophilic polymer layer contains an electrolyte as well as a buffer.

The hydrophilic polymer layer has a thickness of 0.0050–200 μm, and preferably of 0.1–100 μm, and more preferably 1–50 μm.

Various possibilities are available for the manufacture of a hydrophilic polymer layer covalently bonded to the isolator layer.

For the covalent linking it is possible on the one hand to use a bi-functional organosilicon compound which contains on the one hand a group which can be covalently bonded with the isolator layer and on the other a group to which can be covalently bonded either monomers which are to be made to react to form polymers or polymerized material.

Organosilylation reagents used are mentioned in (P. Bergveld, N. F. de Kooy, Ned. Tijdschr. v. Natuurkunde (Dutch Journal of Physics), A46, 22–25 (1980)). Particularly applicable are the organosilicon compounds I and II from table 1.

After the bi-functional organosilicon compound has been covalently bonded to the isolator layer, the hydrophilic polymer layer can be formed by polymerization of monomers geared to the covalently bonded, bi-functional organosilicon compound. Photochemically polymerizable monomers are for instance used in order to enable IC compatible mass production. In the case of the compounds I and II the hydrophilic polymer layer can be formed by polymerization and comprises (a) monomers with the structure formulae:

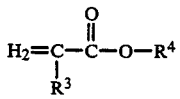

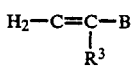

in which $R^3$: is H, alkyl, aryl, halogen
$R^4$: —H, —$R^5$—OH, $R^5$—$NH_2$, $R^5$—SH, $R^5$—$N(CH_3)_2$, $R^5$—sugar, $R^5$—peptide,
$R^5$: alkyl, aryl

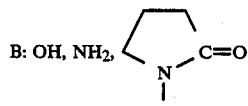

B: OH, $NH_2$, (b) copolymers with additional monomers having the structure formula III, in which $R_4$ is now a $C_1$-$C_{30}$ alkyl group,
(c) mixtures of (co)polymers with a hydrogel, such as gelatin, agar-agar, heparin and polyvinyl pyrrolidone,
(d) copolymers of the monomers III an IV,
(e) mixtures of polymers and/or copolymers of the monomers III and IV,
(f) mixtures of (co)polymers of the monomers III and/or IV with the copolymers as according to point b,
(g) mixtures of the polymers and/or copolymers named under points a–f.

Copolymers of the above mentioned monomers can also be formed with vinyl silanes (Table 1). These materials can be directly linked covalently to the isolator layer.

In this way the hydrophilic polymer layer is applied to the isolator layer.

Water or an aqueous solution is then allowed to penetrate into the hydrophilic layer by means of immersion or addition of a required amount of water.

Finally, the hydrophobic polymer layer is applied over the hydrophilic polymer layer which now contains water. The binding can be performed physically or covalently (chemically).

In the case of a covalent bonding use can be made of a linking agent with the structure formula:

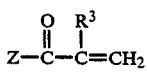

in which $R^3$ has the denotation stated above, and Z=halogen, alkoxy, phenoxy or hydroxy.

The hydrophobic polymer layer is formed by polymerization of monomers containing vinyl groups or by a reaction with "living" polymers.

The use of a linking agent is necessary if, when a covalent bonding is required, it is not possible to make the hydrophobic layer react covalently with functional groups of the hydrophilic polymer layer that are present.

In the case of the above mentioned linking agent, use can then be made of monomers containing vinyls, as referred to in WO 85/04480, and in addition styrene, divinyl benzene, acrylonitrile, vinyl acetate, methyl(meth)acrylate, butyl(meth)acrylate, vinylidene cyanide, chlorostyrene and for example chloromethyl styrene.

It is of course also possible to use silylating reagents as linking agent. (See: Deschler, U., Kleinschmit, P., Panster, P.; Angew. Chemie, 98, 237–253, (1986)). In addition it is also possible to make use of polymers that are provided with reactive silane monomers.

In the case of application of a polymer layer consisting of polyurethanes or polycarbamates or other polymers which are reactive with respect to the hydrophilic layer, it is not necessary to make use of the linking agent.

It is further possible to adhere the hydrophobic polymer layer physically to the hydrophilic polymer layer. this physical binding is realized with the previously described polymers but with omission of the linking agent. Plasticized PVC, siloxane rubbers and polybutadiene can also be used as polymer.

Finally, it is likewise possible to employ so-called "living" polymers.

If no receptor is incorporated in the inert hydrophobic polymer layer, a sensor in which such a FET is included will act as a so-called REFET. This REFET gives a non-ion specific response to variation in the total ion concentration. When the ion strength in the solution to be measured is constant, it therefore acts as a pseudo-reference electrode.

If a receptor is incorporated in the hydrophobic polymer layer, a sensor equipped with same acts as a CHEMFET. The receptor can be bonded covalently or physically into the hydrophobic polymer layer, or entangled therein during polymerization.

The receptor can be an ionophor, such as an antibiotic (e.g. valinomycine), a crown ether, cryptate, podand, hemispherand, cryptohemispherand, spherand.

An $H^+$ sensitive CHEMFET is manufactured by incorporating as ionophor in the inert hydrophobic polymer layer a compound with acidic or basic groups, for instance tridodecyclamine As a result of the choice of a specific receptor and its incorporation in the hydrophobic polymer layer, it is possible to measure selectively the presence and the (thermodynamic) activity in solutions of chemical, and particularly biochemical, compounds such as ions, proteins, substrates, antibodies antigens, hormones, gases, glucose, urea and the like.

Stressed is the fact that the thermodynamic activity of cations as well as anions can of course be determined.

The current invention will be elucidated with reference to a number of examples according to the invention and reference examples, although the invention is in no way limited thereto.

EXAMPLE 1

Placed for two hours in a mixture of methacryloxypropyltrimeth oxysilane (Alfa, US) and toluene which is boiled under reflux conditions is a plaque of semiconductor material for treatment which is provided with an isolator layer consisting of $SiO_2$. After washing with methylethylketone the plaque is dried for 1 hour at 80° C. Hydroxyethylmethacrylate (HEMA; Janssen, Belgium) is then applied in accordance with the so-called dipping method. Polymerization of covalent bonding to the isolator layer are performed photochemically. The polymerization reactions are initiated, using the photoinitiator 2,2-dimethoxy-2-phenylacetophenon (4% by weight; Janssen, Belgium) which is present in the mixture to be polymerized, by radiating the mixture with an ultraviolet source (λmax=360 nm) for 2–10 mins. under an $N_2$ atmosphere.

The thickness of the hydrophilic polymer layer amounts to 15 μm and is determined in accordance with ellipsometry.

The covalently bonded hydrophilic polymer layer is swelled for 30 mins. at room temperature with a solution of 0.1M $KCl+0.025M$ $KH_2PO_4+0.025M$ $Na_2HPO_4$ in water.

A polybutadiene solution (mol. wt. 4300, 99% unsaturated, 25% vinyl and 40% trans-1,4, obtainable from Janssen, Belgium) in tetrahydrofuran is subsequently applied to the water holding, hydrophilic polymer layer and then polymerized photochemically. The thickness of the hydrophobic polymer layer covalently bonded to the hydrophilic, water-holding polymer layer is 10 μm.

EXAMPLE 2

In a manner similar to that described in example 1 a hydrophilic polymer layer is applied to the isolator layer. The outer side of the hydrophilic polymer is then functionalized by reaction with methacryl oxychloride. In this way a part of the hydroxyethyl groups are converted into methacryloxy groups and the hydrophilic polymer layer is swelled in the watery, buffered KCl solution, as described in example 1.

Then applied to the hydrophilic, water-holding polymer layer is a mixture of ACE ($C_9H_{19}C(O)OCH_2CH(OH)CH_2OC(O)CH=CH_2$) and Epocryl (p.R-$C_6H_4-C(CH_3)_2-C_6H_4$p.R; R is $CH_2=C(CH_3)C(O)OCH_2CH(OH)CH_2O-$) (20:80 w/w; obtainable from Shell, the Netherlands) in chloroform, which is subsequently polymerized photochemically. The layer thickness of the hydrophobic polymer layer is 15 μm and it is cross linked with the applied methacryloxy functional groups.

EXAMPLE 3

In the same manner as in example 1 a hydrophilic polymer layer is applied covalently to the isolator layer and swelled in the watery, buffered KCl solution, as described in example 1.

A solution of polyvinylchloride (PVC, obtainable from Fluka, Switzerland, purum; for ion selective electrodes 30% by weight), di-n-butyl phthalate (67% by weight) and valinomycine (obtainable from Fluka, Switzerland, purum pro analysis; 3% by weight) in tetrahydrofuran is then applied. The formed hydrophobic polymer layer has a thickness of 10 μm.

EXAMPLE 4

(reference example)

Placed for two hours in a mixture of methacryloxypropyl trimeth oxysilane and toluene which is boiled under reflux conditions is a plaque of semiconductor material for treatment which is provided with an isolator layer consisting of $SiO_2$. After thorough washing with methylethylketone the plaque is dried for 1 hour at 80° C. This plaque is then placed in a solution of polybutadiene (mol. wt. 3400, 99% unsaturated, 25% vinyl and 40% trans-1,4, obtainable from Janssen, Belgium) in tetrahydrofuran. Photochemical polymerization then takes place. The thickness of the hydrophobic polymer layer covalently applied directly onto the isolator layer is 10 μm.

EXAMPLE 5

(reference example)

In the same maner as in example 4 the silylating process is performed. A mixture of ACE+Epocryl in chloroform is subsequently applied and polymerized photochemically.

The thickness of the hydrophobic polymer layer covalently bonded directly onto the isolator layer is 15 μm.

EXAMPLE 6

(reference example)

After carrying out of the silylating process as according to example 4, a physically bonded hydrophobic polymer layer is bonded directly onto a plaque of semiconductor material that is provided with an isolator layer of $SiO_2$. For this purpose a solution of polyvinylchloride (30% by weight), di-n-butyl phthalate (67% by weight) and valinomycine (3% by weight) is placed in tetrahydrofuran. The layer thickness of this physically bonded hydrophobic polymer layer provided with a receptor is 10 μm.

EXAMPLE 7

(reference example)

Physically bonded onto a plaque of semiconductor material that is provided with an isolator layer consisting of $SiO_2$ is a layer of gelatin from an approx. 3% by weight gelatin solution in water. The thickness of the gelatin layer is 25 μm.

To the gelatin layer is then applied a mixture of ACE+Epocryl (40:60 w/w) in chlorofrm which is photochemically polymerized as previously described. The layer thickness of the hydrophobic polymer layer is 15 μm.

EXAMPLE 8

A mixture of 3 parts by wt. methacryloxypropyltrimethoxysilane and 7 parts by wt. hydroxyethyl methacrylate (HEMA) in toluene is photochemically polymerized. The toluene is distilled off and the product is dissolved in acetone. Applied to the plaque of semiconductor material for treatment that is provided with an isolator layer consisting of $SiO_2$ is a part of the prepared polymer solution in acetone. After evaporation of the acetone the semiconductor material is placed in an oven for 24 hours at 80° C. The thus covalently bonded hydrophilic polymer layer has a thickness of 20 μm. The watery, buffered KCl solution, as described in example 1, is then absorbed by this polymer. A mixture of ACE and Epocryl is then applied, as according to example 2, to this swelled polymer layer and polymerized. The layer thickness amounts to 15 μm.

EXAMPLE 9

A plaque of semiconductor material provided with an isolator layer consisting of $SiO_2$ is, as described in example 1, silylated with methacryloxypropyltrimeth oxysilane. Subsequently a mixture of 50 pts. by wt. hydroxyethylmethacrylate and poly-N-vinyl pyrrolidone (50 pts. by wt.; mol. wt.=360.000; Janssen, Belgium) is applied in accordance with the spin-coating method. Polymerization and covalent binding to the isolator layer is performed photochemically. The thickness of the hydrophilic polymer layer amounts to 25 μm. As is described in example 1, the buffered, watery KCl solution is then absorbed by this polymer. As in example 3, a hydrophobic polymer layer consisting of PVC, di-n-butyl phthalate and valinomycine is then applied. The formed layer has a thickness of 10 μm.

EXAMPLE 10

In the same way as in example 1 a hydrophilic polymer layer is applied to the isolator layer and swelled in the watery, buffered KCl solution, also as described in example 1. Onto the hydrophilic, water-holding polymer layer is then applied and cross linked a mixture of Silopren K 1000 (85% by wt.) cross-linking agent KA-1 (12% by wt.; both from Bayer AG, Leverkusen, Germany) and valinomycine (3% by wt.). The layer thickness amounts to 15 μm.

EXAMPLE 11

(reference example)

In the same manner as in example 4 the silylating process is performed. A mixture of Silopren K 1000 (85% by wt.) cross-linking agent KA-1 (12% by wt.) and valinomycine (3% by wt.) is then applied and cross linked. The layer thickness amounts to 15 μm.

EXAMPLE 12

A plaque of semiconductor material provided with an isolator layer consisting of $SiO_2$ is, as described in example 1, silylated with methacryloxypropyltrimeth oxysilane. Subsequently a mixture of hydroxyethylmethacrylate (60 pts. by wt.) and N-vinyl-2-pyrrolidone (40 pts. by wt.; Janssen, Belgium) is applied in accordance with the dipping method. Polymerization and covalent binding to the isolator layer is performed photochemically. The thickness of the hydrophilic polymer layer amounts to 20 μm. As is described in example 1, the watery, buffered KCl solution is then absorbed by this polymer. A mixture of ACE and Epocryl is then applied, as in example 2, to this swelled polymer layer and photochemically polymerized. The layer thickness amounts to 15 μm.

EXAMPLE 13

A plaque of semiconductor material provided with an isolator layer consisting of $SiO_2$ is, as described in example 1, silylated with metacryloxypropyltrimeth oxysilane. Subsequently N,N-dimethylaminoethylmethacrylate (DMAEMA, Janssen, Belgium) is applied in accordance with the dipping method. Polymerization and covalent binding is performed photochemically. The thickness of the hydrophilic polymer layer amounts to 25 μm. As is described in example 1, a watery, buffered KCl solution is then absorbed by this polymer. A mixture of ACE and Epocryl is then applied, as in example 2, to this swelled polymer layer and photochemically polymerized. The layer thickness amounts to 15 μm.

EXAMPLE 14

As example 1, but here only water is absorbed by the hydrophilic polymer.

EXAMPLE 15

As example 1, but here 0.10M KCl in water is absorbed by the hydrophilic polymer.

EXAMPLE 16

A plaque of semiconductor material provided with an isolator layer consisting of $SiO_2$ is, as described in example 1, silylated with methacryloxypropyltrimeth oxysilane. A hydrophilic polymer layer is then applied which is subsequently functionalized by reaction with methacryl oxychloride, the watery, buffered solution then being absorbed as described in example 1. Onto the hydrophilic polymer layer is then applied a mixture of polybutadiene (for details see example 1) and 4-vinylbenzo-18-crown-6 (5% by wt.) and polymerized photochemically. Layer thickness 10 μm.

Determining of the characteristics of the manufactured REFETs and CHEMFETs

The modified REFETs and CHEMFETs were measured in accordance with the procedure as described by A. van den Berg, P. Bergveld, D. N. Reinhoudt and E. J. R. Sudhölter, Sensors and Actuators 8 129–148 (1985).

The results are shown in table 2.

In addition the reproducibility of the manufactured REFETs and CHEMFETs in mass production is determined and shown in table 3.

A sensor furnished with a REFET such as that of example 7 gave during measurement of pH 7 a continuous increase in the response. After being exposed to this solution for 5 hours a pH response was observed which corresponded to a non-modified ISFET.

A sensor containing a REFET as manufactured in example 2 was found after spending a month in a solution at pH 7 to still display the original, even pH response.

TABLE 1

| Bifunctional organosilicon compounds for covalent bonding of the hydrophilic polymer layer to the isolator layer | |
|---|---|
| Organosilicon compound | Structure formula |
| Vinylsilanes | $\begin{array}{c}(OR)_a\\ R^1{}_b-Si-C=CH_2^*\\ X_c\quad Y\end{array}$ (I) |
| | $\begin{array}{c}(OR)_a\\ R^1{}_b-Si-A-C=CH_2\\ X_c\quad Y\end{array}$ (II) |

Note:
*R, $R^1$: alkyl, aryl
X: halogen, carboxylate, amino, oxim

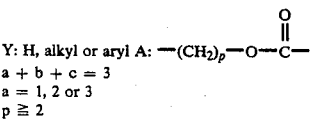

Y: H, alkyl or aryl  A: $-(CH_2)_p-O-\overset{\underset{\|}{O}}{C}-$
a + b + c = 3
a = 1, 2 or 3
p ≧ 2

TABLE 2

| Measured characteristics of REFETs and CHEMFETs | | | |
|---|---|---|---|
| Example | Noise (mV) pH = 7 | Drift[1] (mV/12 hrs) pH = 7 | Hysteresis[2] (mV) |
| 1 | ±0.03 | 10 | 1 |
| 2 | ±0.03 | 4 | 1 |
| 3 | ±0.02 | 8 | 0.5[3] |
| 4 | ±1 | 30 | 5 |
| 5 | ±5 | 35 | 4 |
| 6 | ±0.5 | 12 | 2[3] |
| 7 | —[4] | —[4] | —[4] |
| 8 | ±0.05 | 6 | 1 |
| 9 | ±0.03 | 4 | 0.5[3] |
| 10 | ±0.06 | 10 | 1[3] |
| 11 | ±3 | 40 | 10[3] |
| 12 | ±0.03 | 10 | 1 |
| 13 | ±0.02 | 7 | 0.5 |
| 14 | ±0.5 | 15 | 2 |

TABLE 2-continued

| | Measured characteristics of REFETs and CHEMFETs | | |
|---|---|---|---|
| Example | Noise (mV) pH = 7 | Drift[1] (mV/12 hrs) pH = 7 | Hysteresis[2] (mV) |
| 16 | ±0.04 | 8 | 1[3] |

Notes:
[1]Drift measured after 2 hours stabilization in the solution at pH 7 (beginning of measurement after stabilizing)
[2]Hysteresis measured after a pH scan from pH 2 to pH 10 (scan time 10 min.) followed by a pH scan from pH 10 to pH 2 (scan time 10 min.). Stated is the ΔmV at pH 2.
[3]In this case relates to a titration with KCl from $10^{-4}$ M to $10^{-1}$ M, followed by washing and replacing in a solution of $10^{-4}$ M. ΔmV is stated for $10^{-4}$ M
[4]non-stable

TABLE 3

| Reproducibility of the method | |
|---|---|
| Example | Percentage* |
| 1 | 80 |
| 2 | 90 |
| 3 | 85 |
| 4 | 30 |
| 5 | 10 |
| 6 | 50 |
| 7 | not durable |
| 8 | 85 |
| 9 | 90 |
| 10 | 80 |
| 11 | 40 |
| 12 | 80 |
| 13 | 85 |
| 14 | 80 |
| 15 | 80 |
| 16 | 75 |

Note:
*The reproducibility is shown as the proportion of the number of modified FETs whereby the noise is equal to or better than the value stated in table 2 and the total number of FETs manufactured in this manner.

We claim:

1. Process for manufacturing a REFET or a CHEMFET, comprising:
   (a) covalently bonding a hydrophilic polymer layer to an insulating layer applied to a semiconductor material;
   (b) absorbing water or an aqueous solution into said hydrophilic polymer layer; and
   (c) binding a hydrophobic polymer layer to the water containing hydrophilic polymer layer.

2. Process as claimed in claim 1, in which the water-holding hydrophilic polymer layer also contains an electrolyte.

3. Process as claimed in claim 1, in which the water containing hydrophilic polymer layer also contains a buffer to maintain the hydrophilic polymer layer at a substantially constant pH level.

4. Process as claimed in claim 1, in which the water holding hydrophilic polymer layer has a thickness of 0.0050–200 μm.

5. Process as claimed in claim 2, in which a receptor for a chemical compound is to be measured is incorporated in the hydrophobic polymer layer.

6. Process as claimed in claim 5, in which an ion to be measured with the CHEMFET also forms part of the electrolyte.

7. Process as claimed in claim 1, in which the hydrophilic polymer layer is covalently bonded to the insulating layer by a bi-functional organosilicon compound which is covalently bonded with the isolator layer and which is covalently bonded to the hydrophilic polymer layer.

8. Process as claimed in claim 7, in which the bi-functional organosilicon compound is selected from the group consisting of:

$$\begin{array}{c} (OR)_a \\ R^1{}_b{-}Si{-}C{=}CH_2 \\ X_c \quad\ \ Y \end{array} \quad (I)$$

$$\begin{array}{c} (OR)_a \\ R^1{}_b{-}Si{-}A{-}C{=}CH_2 \\ X_c \quad\quad\ \ Y \end{array} \quad (II)$$

in which
R, R¹: alkyl, aryl
X: halogen, carboxylate, amino, oxim
Y: H, alkyl or aryl $$A: -(CH_2)_p-O-\overset{\overset{\displaystyle O}{\|}}{C}-$$

a+b+c=3
a=1, 2 or 3 and
p≧2.

9. Process as claimed in claim 7, in which the hydrophilic polymer layer is formed by polymerization and is selected from the group consisting of:
   (a) monomers with the structure formulae:

$$H_2C{=}\underset{\underset{\displaystyle R^3}{|}}{C}{-}\overset{\overset{\displaystyle O}{\|}}{C}{-}O{-}R^4 \quad (III)$$

$$H_2C{=}\underset{\underset{\displaystyle R^3}{|}}{C}{-}B \quad (IV)$$

in which
R³: is H, alkyl, aryl, halogen
R⁴: —H, —R⁵—OH, R⁵—NH₂, R⁵—SH, R⁵—N(CH₃)₂, R⁵—sugar, R⁵-peptide,
R⁵: alkyl, aryl B: OH, NH₂, $\begin{array}{c}\diagup\!\!\!\diagdown\\ \diagdown\diagup{-}N{-}\diagdown{C}{=}O\end{array}$ (b) copolymers with additional monomers having the structure formula III in which R₄ is C₁–C₃₀ alkyl group,
   (c) mixtures of (co)polymers with a hydrogel,
   (d) copolymers of the monomers III and IV,
   (e) mixtures of polymers and copolymers of the monomers III and IV,
   (f) mixtures of (co)polymers of the monomers III, and IV, with the copolymers as according to point b,
   (g) mixture of polymers of the monomers III and IV,
   (h) mixtures of copolymers of the monomers III and IV,
   (i) mixtures of (co)polymers of the monomer III with the copolymers as according to point b,
   (j) mixtures of co(polymers) of the monomer IV with the copolymers as according to point b,
   (k) mixtures of the polymers and copolymers named under points a–j.

10. Process as claimed in claim 1, in which the hydrophobic polymer layer is bonded physically to the hydrophilic, water holding polymer layer.

11. Process as claimed in claim 1, in which the hydrophobic polymer layer is bonded covalently to the hydrophilic, water-holding polymer layer.

12. Process as claimed in claim 11, in which a linking agent is allowed to react with the hydrophilic polymer layer and the hydrophobic polymer layer is subsequently bonded to said linking agent.

13. Process as claimed in claim 12, in which the linking agent has the following structure formula:

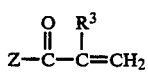

in which $R^3$ is H, alkyl, aryl, halogen and Z=halogen, alkoxy, phenoxy or hydroxy, and the hydrophobic polymer layer is formed by polymerization of monomers containing vinyl groups.

14. Process as claimed in claim 6, in which the receptor is bonded covalently to the hydrophobic polymer layer.

15. REFET or CHEMFET manufactured as claimed in claim 1.

16. Process as claimed in claim 1, in which the water containing hydrophilic polymer layer has a thickness of 0.1–100 μm.

17. Process as claimed in claim 1, in which the water containing hydrophilic polymer layer has a thickness of 1–50 μm.

18. Process as claimed in claim 9, in which the hydrogel is selected from the group consisting of gelatin, agar-agar, heparin and polyvinyl pyrrolidone.

19. Process as claimed in claim 12, in which the linking agent has the following structure formula:

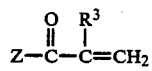

in which $R_3$ is H, alkyl, aryl, halogen and Z=halogen, alkoxy, phenoxy or hydroxy, and the hydrophobic polymer layer is formed by a reaction with "living" polymers.

20. Process as claimed in claim 6, in which the receptor is bonded physically to the hydrophobic polymer layer.

21. Process as claimed in claim 6, in which the receptor is cross linked to the hydrophobic polymer layer.

* * * * *

UNITED STATES PATENT AND TRADEMARK OFFICE
CERTIFICATE OF CORRECTION

PATENT NO. : 4,882,292
DATED : November 21, 1989
INVENTOR(S) : Ernst J. Sudholter, Maria D. Skowronska-Ptasinska, Peter D. Van der Wal, Albert Van den Berg and David N. Reinhoudt It is certified that error appears in the above-identified patent and that said Letters Patent is hereby corrected as shown below:

On the title page:

Under Assignee "Elektronics" should read --Elektronica--.

Column 1 lines 54-55 "Electronics" should read --Elektronica--.

Column 4 Line 64 "of" should read --and--.

Column 8 Line 24 "of" should read --at--.

Column 8 Line 54 "$p \geqq$" should read --$p \geq$--.

Column 8 after Line 14 in Table 2 insert --15  $\pm 0.03$  12  1--.

Claim 5 Line 58 Column 9 after "compound" delete --is--.

Claim 8 Line 26 Column 10 "$p \geqq 2$" should read --$p \geq 2$--.

Signed and Sealed this

Fifteenth Day of January, 1991

Attest:

HARRY F. MANBECK, JR.

*Attesting Officer*     Commissioner of Patents and Trademarks